(12) United States Patent
Nomoto et al.

(10) Patent No.: US 6,914,088 B2
(45) Date of Patent: Jul. 5, 2005

(54) DIACETAL COMPOSITION, POLYOLEFIN NUCLEATING AGENT COMPRISING THE DIACETAL COMPOSITION, POLYOLEFIN RESIN COMPOSITIONS CONTAINING THE DIACETAL COMPOSITION, METHOD FOR MANUFACTURING THE RESIN COMPOSITION, AND MOLDINGS

(75) Inventors: Harutomo Nomoto, Kyoto (JP); Masahide Ishikawa, Uji (JP); Toshiaki Kobayashi, Nara (JP)

(73) Assignee: New Japan Chemical Co., Ltd., Kyoto (JP)

( * ) Notice: Subject to any disclaimer, the term of this patent is extended or adjusted under 35 U.S.C. 154(b) by 0 days.

(21) Appl. No.: 10/196,383

(22) Filed: Jul. 17, 2002

(65) Prior Publication Data

US 2003/0109610 A1 Jun. 12, 2003

Related U.S. Application Data

(63) Continuation of application No. PCT/JP02/02876, filed on Mar. 26, 2002.

(30) Foreign Application Priority Data

Mar. 27, 2001 (JP) ........................................ 2001-090550

(51) Int. Cl.[7] .................................................. C08K 5/15
(52) U.S. Cl. ...................................... 524/108; 524/109
(58) Field of Search ................................. 524/108, 109

(56) References Cited

U.S. PATENT DOCUMENTS

| 5,049,605 A | 9/1991 | Rekers ........................ 524/108 |
| 6,043,303 A | 3/2000 | Kobayashi et al. ......... 524/109 |

FOREIGN PATENT DOCUMENTS

| EP | 0964029 | 12/1999 |
| EP | 0969036 | 1/2000 |
| WO | WO99/18108 | 4/1999 |

OTHER PUBLICATIONS

European Search Report dated Feb. 16, 2005.

*Primary Examiner*—Peter D. Mulcahy
(74) *Attorney, Agent, or Firm*—Armstrong, Kratz, Quintos, Hanson & Brooks, LLP

(57) ABSTRACT

Disclosed are a granular or powdery diacetal composition comprising (A) a diacetal such as 1,3:2,4-O-dibenzylidene-D-sorbitol, (B) a sulfuric ester salt and (C) an aliphatic monocarboxylic acid, components (B) and (C) being uniformly dispersed in the particles of the granular or powdery diacetal composition, and component (B) being present in a proportion of 0.1 to 3 wt % and component (C) being present in a proportion of 0.3 to 5 wt %, and the total amount of component (B) and component (C) being not more than 7 wt %, based on the diacetal composition; a polyolefin resin composition comprising the diacetal composition and a polyolefin resin; a process for preparing the resin composition; and a molding prepared by molding the polyolefin resin composition.

13 Claims, 2 Drawing Sheets

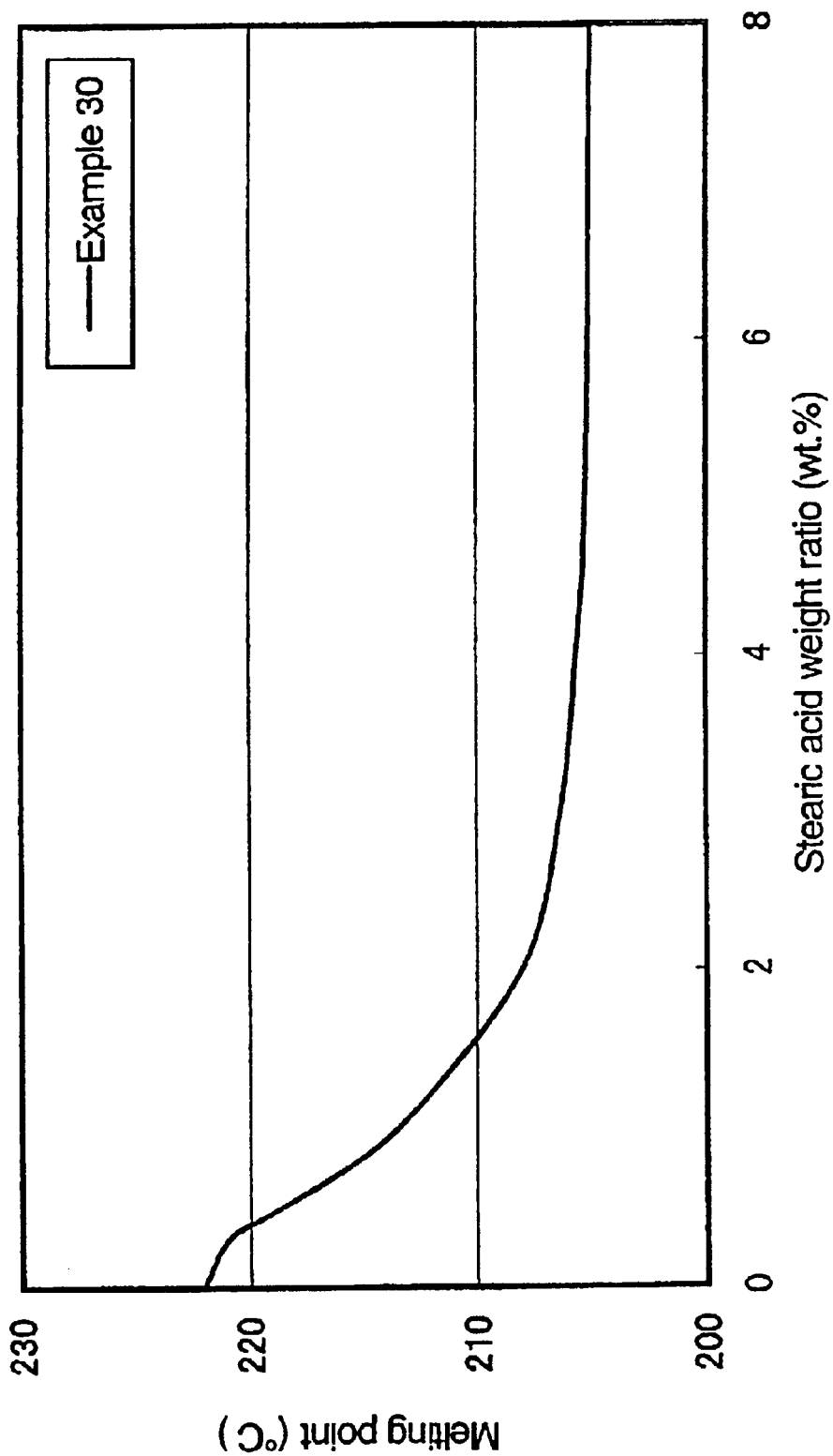

DIACETAL COMPOSITION, POLYOLEFIN NUCLEATING AGENT COMPRISING THE DIACETAL COMPOSITION, POLYOLEFIN RESIN COMPOSITIONS CONTAINING THE DIACETAL COMPOSITION, METHOD FOR MANUFACTURING THE RESIN COMPOSITION, AND MOLDINGS

This application is a continuation of international application PCT/JP02/02876 filed on Mar. 26, 2002.

TECHNICAL FIELD

This invention relates to a diacetal composition, a polyolefin resin nucleating agent containing this composition, a polyolefin resin composition containing this composition, and moldings thereof.

BACKGROUND ART

Diacetals such as dibenzylidene sorbitols and nuclear-substituted derivatives thereof are useful compounds that are widely used as nucleating agents for polyolefin resins, gelling agents for various fluids, and so on. For taking full advantage of the characteristics of these compounds, the diacetal must first be dissolved or uniformly dispersed in a molten polyolefin resin or a fluid. However, these diacetals have strong self-agglomeration properties and also have a high melting point, so that uniformly dissolving or dispersing them is not easy in an industrial setting. Accordingly, the solubility and dispersibility of diacetals must be improved by one means or another.

There have been various proposals up to now aimed at ameliorating the above problems. Examples include a method in which a diacetal is treated at a temperature over its melting point or melting temperature, and a method in which a diacetal is reduced to an ultrafine powder in an effort to increase its dispersibility and make it more readily soluble (Japanese Unexamined Patent Publication No. H6-145431). Nevertheless, (1) the first method, in which a diacetal is treated at a high temperature, causes the diacetal to undergo thermal decomposition, and therefore the nucleating agent does not reach its full performance potential, and there are also problems with coloration, odor, and so forth. (2) The second method (Japanese Unexamined Patent Publication No. H6-145431) involving reducing a diacetal to an ultrafine powder to improve its dispersibility and solubility leads to serious industrial problems such as dust explosion, an adverse effect on the workplace environment, re-agglomeration during storage, difficulty of transport (in particular, the difficulty of transport when discharged from a stock tank and difficulty of transport through pipes), decreased fluidity and other factors that make the material more difficult to work with. Also, this method requires expensive special pulverization equipment, and these and other problems have yet to be satisfactorily solved.

Another known method involves uniformly dispersing a substance for depressing the melting point in diacetal particles, thereby lowering the melting point of the diacetal (WO99/18108). This technique does not require that the diacetal be treated at high temperature or reduced to an ultrafine powder, and is an effective way to improve the solubility and dispersibility of a diacetal. However, there is still a need for (a) a further lowering of the diacetal melting point and (b) a lowering of the diacetal melting point to a practical level by using only a small amount of melting point depressant.

It is an object of the present invention to solve these problems by providing a diacetal composition with markedly improved solubility and dispersibility in various liquids and in various molten resins.

In particular, it is an object of the present invention to provide a diacetal composition which has improved solubility, dispersibility and storage stability of the diacetal, which can give a polyolefin resin molding with a less undispersed substance content and excellent transparency, and which contains a melting point depressing substance only in a small amount.

DISCLOSURE OF THE INVENTION

The inventors carried out intensive research to achieve the above object. In the above-mentioned publication WO99/18108, various compounds are used in a large quantity (about 10 wt % of the diacetal composition) for the purpose of depressing the melting point, and the effect of the diacetal composition of this publication as a nucleating agent may be diminished as compared with the same amount of an untreated diacetal as a polyolefin resin additive.

Also, in WO99/18108, L-tartaric acid, succinic acid, citric acid, DL-malic acid and other such aliphatic dibasic acids or sodium lauryl sulfate are mentioned as melting point depressants that greatly lower the melting point when added in just a small amount. However, research by the inventors has revealed that a diacetal composition in which the above-mentioned L-tartaric acid, succinic acid, citric acid, DL-malic acid or other such aliphatic dibasic acid is uniformly dispersed in a diacetal does not have sufficient storage stability, and particularly storage stability at high temperature, and therefore cannot be considered wholly satisfactory. Also, when used as a polyolefin resin nucleating agent, a diacetal composition in which sodium laurylsulfate is uniformly dispersed in a diacetal does have good dispersibility if the molding resin temperature is close to or higher than the melting point of this diacetal composition, but dispersibility will not necessarily be adequate if the molding resin temperature is lower than the melting point of this diacetal composition. Specifically, it was found that such a composition is not necessarily satisfactory for applications that require low temperature processing.

Accordingly, it has been considered impossible to develop a melting point depressant which has an excellent melting point depressing effect when added in a small amount, and which has excellent storage stability and low temperature processing characteristics.

As a result of further investigation, however, it was discovered that when a specific anionic surfactant and a specific aliphatic monocarboxylic acid are used together in specific amounts as melting point depressants and are uniformly dispersed in a diacetal that is in a swollen or dissolved state, and the composition is then dried, the resulting diacetal composition exhibits dispersibility/solubility and melting point depression that could not have been expected from the prior art, even though the resulting diacetal composition contains only a small amount of the melting point depressant.

More specifically, it was discovered that when a specific anionic surfactant and a specific aliphatic monocarboxylic acid are used together, (a) the melting point of the diacetal lowers more than when either one of these compounds is used alone, (b) the dispersibility in a polyolefin resin of the diacetal composition in which both compounds are used will be better than that of a diacetal composition that is obtained using either compound alone that exhibits about the same melting point depressing effect, (c) the melting point of the diacetal lowers at a small added amount, and (d) the storage stability is markedly improved.

The present invention was accomplished based on this finding.

Specifically, the present invention provides the following diacetal composition, polyolefin resin nucleating agent containing this composition, polyolefin resin composition containing this composition, and moldings thereof.

Item 1. A granular or powdery diacetal composition comprising:

(A) at least one diacetal represented by the formula (1)

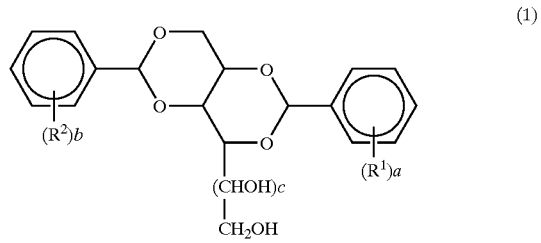

(1)

wherein $R^1$ and $R^2$ are the same or different and each represents a hydrogen atom, a $C_1$ to $C_4$ alkyl group, a $C_1$ to $C_4$ alkoxy group, a $C_1$ to $C_4$ alkoxycarbonyl group or a halogen atom; a and b each represents an integer of 1 to 5; c is 0 or 1; when a is 2, the two $R^1$ groups taken together with the benzene ring to which they are linked may form a tetralin ring; and when b is 2, the two $R^2$ groups taken together with the benzene ring to which they are linked may form a tetralin ring);

(B) at least one anionic surfactant, i.e., at least one sulfuric ester salt selected from the group consisting of $C_6$ to $C_{30}$ saturated or unsaturated aliphatic alcohol sulfuric ester salts, polyoxyethylene alkyl ($C_8$ to $C_{22}$) or alkenyl ($C_8$ to $C_{22}$) ether sulfuric ester salts in which the number of moles of ethylene oxide added is 1 to 8, polyoxyethylene alkyl ($C_8$ to $C_{22}$) phenyl ether sulfuric ester salts in which the number of moles of ethylene oxide added is 1 to 10, sulfuric ester salts of polyhydric alcohol fatty acid partial esters formed from a $C_3$ to $C_6$ polyhydric alcohol and a $C_8$ to $C_{22}$ saturated or unsaturated fatty acid, and $C_8$ to $C_{22}$ saturated or unsaturated fatty acid monoalkanol ($C_2$ to $C_6$) amide sulfuric ester salts, wherein the sulfuric ester salt is lithium salt, sodium salt, potassium salt and/or ammonium salt; and (C) at least one aliphatic monocarboxylic acid which may have at least one hydroxyl group in the molecule, components (B) and (C) being uniformly dispersed in the particles of the granular or powdery diacetal composition, and component (B) being present in a proportion of 0.1 to 3 wt % and component (C) being present in a proportion of 0.3 to 5 wt %, and the total amount of component (B) and component (C) being not more than 7 wt %, based on the diacetal composition.

Item 2 The diacetal composition according to item 1 above, wherein the weight ratio of component (B): component (C) is 1:0.3 to 4.

Item 3 The diacetal composition according to item 1 above, wherein component (C) is a $C_{10}$ to $C_{32}$ aliphatic monocarboxylic acid.

Item 4 The diacetal composition according to any of items 1 to 3 above, wherein component (B) is at least one sulfuric ester salt selected from the group consisting of lauryl sulfate salts, stearyl sulfate salts, oleyl sulfate salts, polyoxyethylene (the number of moles of ethylene oxide added=2 to 3 moles) lauryl ether sulfate salts, polyoxyethylene (the number of moles of ethylene oxide added=2 to 3 moles) stearyl ether sulfate salts, polyoxyethylene (the number of moles of ethylene oxide added=2 to 3 moles) nonylphenyl ether sulfate salts, polyoxyethylene (the number of moles of ethylene oxide added=2 to 3 moles) dodecylphenyl ether sulfate salts, monolauric acid glyceryl sulfate salts, monostearic acid glyceryl sulfate salts, lauric acid monoethanolamide sulfuric ester salts, stearic acid monoethanolamide sulfuric ester salts, and oleic acid monoethanolamide sulfuric ester salts, wherein the sulfuric ester salt is a lithium salt, a sodium salt, or a potassium salt.

Item 5 The diacetal composition according to any of items 1 to 4 above, wherein component (C) is at least one aliphatic monocarboxylic acid selected from the group consisting of capric acid, lauric acid, myristic acid, palmitic acid, stearic acid, 12-hydroxystearic acid, isostearic acid, eicosanoic acid, behenic acid, docosahexanoic acid, montanic acid, oleic acid, linoleic acid, linolenic acid, eleostearic acid, ricinoleic acid, and erucic acid.

Item 6 The diacetal composition according to item 1 or 2 above, wherein component (A) is at least one member selected from the group consisting of 1,3:2,4-O-dibenzylidene-D-sorbitol, 1,3:2,4-bis-O-(p-methylbenzylidene)-D-sorbitol, 1,3:2,4-bis-O-(p-ethylbenzylidene)-D-sorbitol, and 1,3:2,4-bis-O-(3,4-dimethylbenzylidene)-D-sorbitol, component (B) is at least one member selected from the group consisting of lithium lauryl sulfate, sodium lauryl sulfate, potassium lauryl sulfate, lithium polyoxyethylene (the number of moles of ethylene oxide added=2 to 3 moles) lauryl ether sulfate, sodium polyoxyethylene (the number of moles of ethylene oxide added=2 to 3 moles) lauryl ether sulfate, and potassium polyoxyethylene (the number of moles of ethylene oxide added=2 to 3 moles) lauryl ether sulfate, and component (C) is at least one member selected from the group consisting of lauric acid, palmitic acid, myristic acid, stearic acid, 12-hydroxystearic acid and oleic acid.

Item 7 A polyolefin resin nucleating agent comprising the diacetal composition according to any of items 1 to 6 above.

Item 8 A polyolefin resin composition prepared by blending a polyolefin resin with the polyolefin resin nucleating agent according to item 7.

Item 9 The polyolefin resin composition according to item 8 above, wherein the polyolefin resin nucleating agent according to item 7 above is used in an amount of 0.01 to 5 weight parts per 100 weight parts of the polyolefin resin.

Item 10 A polyolefin resin molding obtainable by molding the polyolefin resin composition according to item 8 above.

Item 11 A polyolefin resin molding obtainable by molding the polyolefin resin composition according to item 9 above.

Item 12 The polyolefin resin molding according to item 10 or 11 above, in which substantially no undispersed nucleating agent is present.

Item 13 A method for manufacturing polyolefin resin pellets, comprising uniformly agitating a mixture containing a polyolefin resin and the polyolefin resin nucleating agent according to item 7 above at a temperature not lower than the melting temperature of the polyolefin resin and not higher than the melting point of the polyolefin resin nucleating agent, and pelletizing the melt thus obtained.

BRIEF DESCRIPTION OF THE DRAWINGS

FIG. 2 is a graph showing the results of measuring the melting point in Example 30.

DETAILED DESCRIPTION OF THE INVENTION

Component (A): Diacetal

Figure 1:
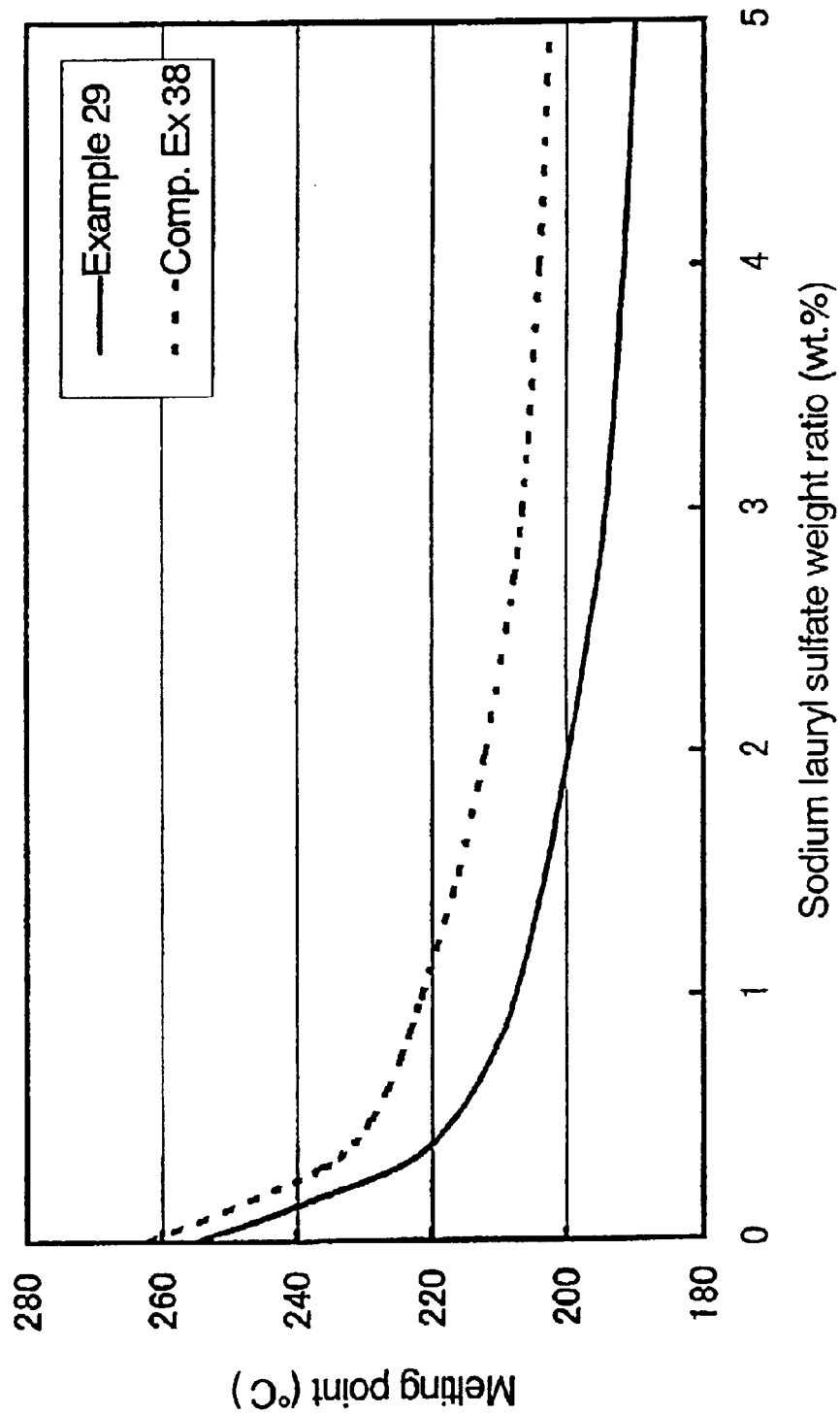
FIG. 1 is a graph showing the results of measuring the melting point in Example 29 and Comparative Example 38.

In the formula (1), examples of $C_1$ to $C_4$ alkyl groups represented by $R^1$ and $R^2$ include methyl group, ethyl group, propyl group, isopropyl group, butyl group, etc. Examples of $C_1$ to $C_4$ alkoxy groups include methoxy group, ethoxy group, propoxy group, isopropoxy group, butoxy group, etc. Examples of $C_1$ to $C_4$ alkoxycarbonyl groups include methoxycarbonyl group, ethoxycarobonyl group, propoxycarbonyl group, isopropoxycarbonyl group, etc. Examples of halogen atoms include fluorine atom, chlorine atom, bromine atom, etc.

a and b are each an integer of 1 to 5, preferably 1, 2 or 3. c is preferably 1. There are no particular restrictions on the position of the substituents represented by $R^1$ and $R^2$, but examples include o-, m- and p-positions when a and b are each 1, and 2,4-, 3,4- or 3,5-positions when a and b are each 2, or 2,4,5- or 3,4,5-positions when a and b are each 3.

All of the diacetals represented by the formula (1) above are known or can be readily prepared by a known process, such as those set forth in Japanese Examined Patent Publication S48-43748 and Japanese Unexamined Patent Publications Nos. S53-5165, S57-185287 and H2-231488.

The following are typical examples of the diacetal represented by the formula (1).

1,3:2,4-O-dibenzylidene-D-sorbitol, 1,3:2,4-bis-O-(o-methylbenzylidene)sorbitol, 1,3:2,4-bis-O-(m-methylbenzylidene)-D-sorbitol, 1,3:2,4-bis-O-(m-ethylbenzylidene)-D-sorbitol, 1,3:2,4-bis-O-(m-isopropylbenzylidene)-D-sorbitol, 1,3:2,4-bis-O-(m-n-propylbenzylidene)-D-sorbitol, 1,3:2,4-bis-O-(m-n-butylbenzylidene)-D-sorbitol, 1,3:2,4-bis-O-(p-methylbenzylidene)-D-sorbitol, 1,3:2,4-bis-O-(p-ethylbenzylidene)-D-sorbitol, 1,3:2,4-bis-O-(p-isopropylbenzylidene)-D-sorbitol, 1,3:2,4-bis-O-(p-n-propylbenzylidene)-D-sorbitol, 1,3:2,4-bis-O-(p-n-butylbenzylidene)-D-sorbitol, 1,3:2,4-bis-O-(2,3-dimethylbenzylidene)-D-sorbitol, 1,3:2,4-bis-O-(2,4-dimethylbenzylidene)-D-sorbitol, 1,3:2,4-bis-o-(2,5-dimethylbenzylidene)-D-sorbitol, 1,3:2,4-bis-O-(3,4-dimethylbenzylidene)-D-sorbitol, 1,3:2,4-bis-O-(3,5-dimethylbenzylidene)-D-sorbitol, 1,3:2,4-bis-o-(2,3-diethylbenzylidene)-D-sorbitol, 1,3:2,4-bis-o-(2,4-diethylbenzylidene)-D-sorbitol, 1,3:2,4-bis-O-(2,5-diethylbenzylidene)-D-sorbitol, 1,3:2,4-bis-O-(3,4-diethylbenzylidene)-D-sorbitol, 1,3:2,4-bis-O-(3,5-diethylbenzylidene)-D-sorbitol, 1,3:2,4-bis-O-(2,4,5-trimethylbenzylidene)-D-sorbitol, 1,3:2,4-bis-O-(3,4,5-trimethylbenzylidene)-D-sorbitol, 1,3:2,4-bis-O-(2,4,5-triethylbenzylidene)-D-sorbitol, 1,3:2,4-bis-O-(3,4,5-triethylbenzylidene)-D-sorbitol, 1,3:2,4-bis-O-(p-methyloxycarbonylbenzylidene)-D-sorbitol, 1,3:2,4-bis-O-(p-ethyloxycarbonylbenzylidene)-D-sorbitol, 1,3:2,4-bis-O-(p-isopropyloxycarbonylbenzylidene)-D-sorbitol, 1,3:2,4-bis-O-(o-n-propyloxycarbonylbenzylidene)-D-sorbitol, 1,3:2,4-bis-O-(o-n-butylbenzylidene)-D-sorbitol, 1,3:2,4-bis-O-(o-chlorobenzylidene)-D-sorbitol, 1,3:2,4-bis-O-(p-chlorobenzylidene)-D-sorbitol, 1,3:2,4-bis-O-[(5,6,7,8-tetrahydro-1-naphthalene)-1-methylene)]-D-sorbitol, 1,3:2,4-bis-O-[(5,6,7,8-tetrahydro-2-naphthalene)-1-methylene]-D-sorbitol, 1,3-O-benzylidene-2,4-O-p-methylbenzylidene-D-sorbitol, 1,3-O-p-methylbenzylidene-2,4-O-benzylidene-D-sorbitol, 1,3-O-benzylidene-2,4-O-p-ethylbenzylidene-D-sorbitol, 1,3-O-p-ethylbenzylidene-2,4-O-benzylidene-D-sorbitol, 1,3-O-benzylidene-2,4-O-p-chlorobenzylidene-D-sorbitol, 1,3-O-p-chlorobenzylidene-2,4-O-benzylidene-D-sorbitol, 1,3-O-benzylidene-2,4-O-(2,4-dimethylbenzylidene)-D-sorbitol, 1,3-O-(2,4-dimethylbenzylidene)-2,4-O-benzylidene-D-sorbitol, 1,3-O-benzylidene-2,4-O-(3,4-dimethylbenzylidene)-D-sorbitol, 1,3-O-(3,4-dimethylbenzylidene)-2,4-O-benzylidene-D-sorbitol, 1,3-O-p-methyl-benzylidene-2,4-O-p-ethylbenzylidene sorbitol, 1,3-p-ethyl-benzylidene-2,4-p-methylbenzylidene-D-sorbitol, 1,3-O-p-methyl-benzylidene-2,4-O-p-chlorobenzylidene-D-sorbitol, and 1,3-O-p-chloro-benzylidene-2,4-O-p-methylbenzylidene-D-sorbitol. These can be used singly or at least two of them may be used as suitably combined.

Of these, preferable are more effective compounds such as 1,3:2,4-O-dibenzylidene-D-sorbitol, 1,3:2,4-bis-O-(o-methylbenzylidene)sorbitol, 1,3:2,4-bis-O-(p-methylbenzylidene)-D-sorbitol, 1,3:2,4-bis-O-(p-ethylbenzylidene)-D-sorbitol, 1,3:2,4-bis-o-(p-isopropylbenzylidene)-D-sorbitol, 1,3:2,4-bis-O-(p-n-propylbenzylidene)-D-sorbitol, 1,3:2,4-bis-O-(p-n-butylbenzylidene)-D-sorbitol, 1,3:2,4-bis-O-(2,4-dimethylbenzylidene)-D-sorbitol, 1,3:2,4-bis-O-(3,4-dimethylbenzylidene)-D-sorbitol, 1,3:2,4-bis-O-(3,5-dimethylbenzylidene)-D-sorbitol, 1,3:2,4-bis-O-(2,4,5-trimethylbenzylidene)-D-sorbitol, 1,3:2,4-bis-O-(p-methyloxycarbonylbenzylidene)-D-sorbitol, 1,3:2,4-bis-O-[(5,6,7,8-tetrahydro-1-naphthalene)-1-methylene)]-D-sorbitol, 1,3:2,4-bis-O-[(5,6,7,8-tetrahydro-2-naphthalene)-1-methylene]-D-sorbitol, 1,3-O-benzylidene-2,4-O-p-methylbenzylidene-D-sorbitol, 1,3-O-p-methylbenzylidene-2,4-O-benzylidene-D-sorbitol, 1,3-O-benzylidene-2,4-O-(2,4-dimethylbenzylidene)-D-sorbitol, 1,3-O-(2,4-dimethylbenzylidene)-2,4-O-benzylidene-D-sorbitol, 1,3-O-benzylidene-2,4-O-(3,4-dimethylbenzylidene)-D-sorbitol, and 1,3-O-(3,4-dimethylbenzylidene)-2,4-O-benzylidene-D-sorbitol. These may be used singly or at least two of them may be used as suitably combined.

Of these, 1,3:2,4-O-dibenzylidene-D-sorbitol, 1,3:2,4-bis-o-(p-methylbenzylidene)-D-sorbitol, 1,3:2,4-bis-O-(p-ethylbenzylidene)-D-sorbitol, and 1,3:2,4-bis-O-(3,4-dimethylbenzylidene)-D-sorbitol are particularly preferable.

There are no particular restrictions on the crystal form of the diacetal as long as the effect of the invention can be achieved, and any crystal form can be used, such as hexagonal, monoclinic, and cubic. These crystals are known or can be manufactured by a known method.

The diacetal used in the present invention may be one in which the purity of the 1,3:2,4-compound represented by the formula (1) is 100%, but may also be one containing a small amount of impurities. Generally, the diacetal is one in which the purity of the 1,3:2,4-compound represented by the formula (1) is at least 90 wt %, preferably 95 wt %, and more preferably at least 97 wt %.

Acetal compounds formed by the condensation reaction of a pentahydric or hexahydric alcohol such as D-sorbitol and a substituted or unsubstituted aromatic aldehyde in the synthesis of the diacetal represented by the the formula (1) include the 1,3:2,4-diacetals represented by the the formula (1), as well as other acetal compounds (by-products), including monoacetals such as a 1,2-compound, 3,4-compound, 2,4-compound or 1,3-compound, triacetals such as a 1,3:2, 4:5,6-compound or 1,2:3,4:5,6-compound, and diacetal isomers such as a 1,2:3,4-isomer.

The diacetal composition of the present invention may contain, in addition to the diacetal represented by the formula (1), at least one member of monoacetals, triacetals, or diacetal isomers, which are impurities thereof. In this case, there would be no particular problems if the total amount of these impurities is not more than 10 wt %, preferably 0.05 to 10 wt %, and more preferably 0.1 to 5 wt %, and particularly 0.1 to 3 wt % or less, relative to the total amount of the acetals (total amount of 1,3:2,4-diacetal represented by the formula (1), monoacetals, triacetals, and isomers of the diacetal). The presence of such impurities is actually beneficial from the standpoint of lowering the melting point of the diacetal composition of the present invention. Still, the nucleating agent characteristics tends to deteriorate if the amount is 10 wt % or more.

Component (B): Anionic Surfactant

Examples of the sulfuric ester salt used as an anionic surfactant in the present invention include $C_6$ to $C_{30}$, preferably $C_{10}$ to $C_{20}$, saturated or unsaturated aliphatic alcohol sulfuric ester salts; polyoxyethylene alkyl ($C_8$ to $C_{22}$, preferably $C_{10}$ to $C_{22}$) or alkenyl ($C_8$ to $C_{22}$, preferably $C_{10}$ to $C_{22}$) ether sulfuric ester salts in which the number of moles of ethylene oxide added is 1 to 8, preferably 2 to 5; polyoxyethylene alkyl ($C_8$ to $C_{22}$, preferably $C_9$ to $C_{20}$) phenyl ether sulfuric ester salts in which the number of moles of ethylene oxide added is 1 to 8, preferably 2 to 5; sulfuric ester salts of polyhydric alcohol fatty acid partial esters formed from a $C_3$ to $C_6$, preferably $C_3$ or $C_4$, polyhydric alcohol and a $C_8$ to $C_{22}$, preferably $C_{10}$ to $C_{20}$, saturated or unsaturated fatty acid; and $C_8$ to $C_{22}$, preferably $C_{10}$ to $C_{20}$, saturated or unsaturated fatty acid alkanol($C_2$ to $C_6$, preferably $C_2$ to $C_4$) amide sulfuric ester salts.

The sulfuric ester salt is a lithium salt, sodium salt, potassium salt, or ammonium salt.

Of the above, the following anionic surfactants are preferred.

A saturated or unsaturated aliphatic alcohol sulfuric ester salt represented by the formula (a):

$$R^a\text{—}OSO_3M \quad (a)$$

wherein $R^a$ is a $C_6$ to $C_{30}$, preferably $C_{10}$ to $C_{20}$, saturated or unsaturated aliphatic group (particularly an alkyl or alkenyl group), and M is Li, Na, K or $NH_4$.

A polyoxyethylene alkyl or alkenyl ether sulfuric ester salt represented by the formula (b):

$$R^bO\text{—}(CH_2CH_2O)_m\text{—}SO_3M \quad (b)$$

wherein $R^b$ is an alkyl group ($C_8$ to $C_{22}$, preferably $C_{10}$ to $C_{22}$) or alkenyl group ($C_8$ to $C_{22}$, preferably $C_{10}$ to $C_{22}$), m is an integer of 1 to 8, preferably 2 to 5, and M is Li, Na, K or $NH_4$.

A polyoxyethylene alkyl or alkylphenyl ether sulfuric ester salt represented by the formula (c):

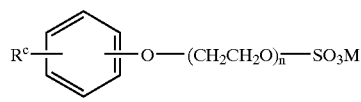

(c)

wherein $R^c$ is an alkyl group ($C_8$ to $C_{22}$, preferably $C_8$ to $C_{20}$), n is an integer of 1 to 8, preferably 2 to 5, and M is Li, Na, K or $NH_4$.

A sulfuric ester salt of a polyhydric alcohol fatty acid partial ester formed from a $C_3$ to $C_6$, preferably $C_3$ or $C_4$, dihydric to tetrahydric alcohol and a $C_8$ to $C_{22}$, preferably $C_{10}$ to $C_{20}$, saturated or unsaturated fatty acid, and particularly a sulfuric ester salt of a mono- or diester of glycerol and a $C_8$ to $C_{22}$, preferably $C_{10}$ to $C_{20}$, saturated or unsaturated fatty acid (the salt is a Li, Na, K or $NH_4$ salt).

Specific examples include sodium lauryl sulfate, sodium stearyl sulfate, sodium oleyl sulfate, sodium polyoxyethylene (the number of moles of ethylene oxide added=2 to 3 moles) lauryl ether sulfate, sodium polyoxyethylene (the number of moles of ethylene oxide added=2 to 3 moles) stearyl ether sulfate, sodium polyoxyethylene (the number of moles of ethylene oxide added=2 to 3 moles) nonylphenyl ether sulfate, sodium polyoxyethylene (the number of moles of ethylene oxide added=2 to 3 moles) dodecylphenyl ether sulfate, sodium monolauric acid glyceryl sulfate, sodium monostearic acid glyceryl sulfate, sodium lauric acid monoethanolamide sulfate, sodium stearic acid monoethanolamide sulfate, and sodium oleic acid monoethanolamide sulfate.

Preferred examples include sodium lauryl sulfate, sodium stearyl sulfate, sodium oleyl sulfate, sodium polyoxyethylene (the number of moles of ethylene oxide added=2 to 3 moles) lauryl ether sulfate, sodium polyoxyethylene (the number of moles of ethylene oxide added=2 to 3 moles) stearyl ether sulfate, sodium polyoxyethylene (the number of moles of ethylene oxide added=2 to 3 moles) nonylphenyl ether sulfate, and sodium polyoxyethylene (the number of moles of ethylene oxide added=2 to 3 moles) dodecylphenyl ether sulfate. In addition to the above sodium salts, other examples of the above-mentioned sulfuric ester salts include lithium salts, potassium salts, and ammonium salts.

The above-mentioned sulfuric ester salt is a lithium salt, sodium salt, potassium salt or ammonium salt, among which a lithium salt, a sodium salt or a potassium salt is recommended. The anionic surfactants listed above can be used singly or at least two of them may be used as suitably combined.

Component (C): Aliphatic Monocarboxylic Acid

Examples of the aliphatic monocarboxylic acid that may have at least one hydroxyl group in the molecule in the present invention include $C_{10}$ to $C_{32}$, preferably $C_{12}$ to $C_{22}$, aliphatic monocarboxylic acids that may have one or two, particularly one, hydroxyl group in the molecule. These can be used singly or at least two of them may be used as suitably combined.

Specific examples include, e.g., capric acid, lauric acid, myristic acid, palmitic acid, stearic acid, 12-hydroxystearic acid, isostearic acid, eicosanoic acid, behenic acid, docosahexanoic acid and montanic acid which are saturated fatty acids, and oleic acid, linoleic acid, linolenic acid, eleostearic acid, ricinoleic acid and erucic acid which are unsaturated fatty acids. Of these, the use of lauric acid, myristic acid, palmitic acid, stearic acid, and 12-hydroxystearic acid are recommended.

Diacetal Composition of the Present Invention

The diacetal composition of the present invention is composed of a diacetal represented by the above-mentioned formula (1) (component (A)), an anionic surfactant (component (B)), and an aliphatic monocarboxylic acid (component (C)), wherein component (B) and component (C) are uniformly dispersed in the particles of the diacetal composition.

The term "uniformly dispersed in the particles of the diacetal composition" as used in this specification refers to a state of being uniformly dispersed in the interior and on the surface of the diacetal particles, or to a state of being uniformly dispersed between the fibrous diacetal crystals that make up the diacetal particles.

In the diacetal composition, the effect of depressing the melting point is greatly affected by the anionic surfactant (component (B)), but is affected less by the aliphatic monocarboxylic acid (component (C)). As is clear from the results of the comparative examples which will be given below, the melting point depression resulting from the use of component (B) alone or from the use of component (C) alone is about 15 to 50° C. with component (B) and about 2 to 10° C. with component (C), relative to the melting point of the diacetal itself. Assuming that there is an additivity in the melting point depression, it is predicted that the melting point depression resulting from using component (B) in combination with component (C) would be about 17 to 60° C.

Actually, however, the combined use of component (B) and component (C) unexpectedly produces an effect that exceeds the degree of melting point depression predicted based on the additivity in using component (B) and component (C), and the present diacetal composition generally achieves a melting point depression of at least 20° C., particularly at least 50° C., and sometimes 80° C. or more, compared to the melting point of the diacetal itself contained in said composition. This was quite surprising.

This effect produced by the combined use cannot be completely explained merely by freezing point depression, and the mechanism thereof remains to be clarified.

The amount of the anionic surfactant (component (B)) used in the present invention is 0.1 to 3 wt %, preferably 0.5 to 3 wt %, more preferably 0.5 to 2 wt %, based on the diacetal composition If the amount of component (B) is less than 0.1 wt %, the melting point depression resulting from the use thereof in combination with component (C) tends to be inadequate, and also the effect of depressing the melting point of component (A) tends to be inadequate. On the other hand, use of component (B) in an amount exceeding 3 wt % usually fails to achieve further improvement in the effect of depressing the melting point of component (A), and tends to diminish the nucleating agent effect to be exerted on polyolefin resins, and especially tends to diminish clarity.

The amount of the aliphatic monocarboxylic acid (component (C)) used in the present invention is 0.3 to 5 wt %, preferably 0.5 to 4 wt %, based on the diacetal composition. If the amount of component (C) is less than 0.3 wt %, the improvement in dispersibility and the melting point depression resulting from the use thereof in combination with component (B), anionic surfactant, tend to be inadequate. On the other hand, the use of component (C) in an amount exceeding 5 wt % usually fails to achieve further improvement in the effect resulting from the use thereof in combination with component (B) and in the effect of depressing the melting point of component (A), and tends to diminish the nucleating agent effect to be exerted on polyolefin resins.

The total amount of component (B)+component (C) is 7 wt % or less, preferably 5 wt % or less. If the total amount exceeds 7 wt %, nucleating agent effect to be exerted on polyolefin resins tends to decrease.

The weight ratio of component (B): component (C) is preferably between 1:0.3 to 4, more preferably 1:0.5 to 3, most preferably 1:1 to 3. Within this range, the effect produced by using component (B) together with component (C) is readily obtained, and superior effect is obtained by such combined use.

As stated above, in the diacetal composition of the present invention, component (B) is present in a proportion of 0.1 to 3 wt %, preferably 0.5 to 3 wt %, more preferably 0.5 to 2 wt %, and component (C) is present in a proportion of 0.3 to 5 wt %, preferably 0.5 to 4 wt % (with the total amount of component (B)+component (C) being not more than 7 wt %), based on the diacetal composition, with the balance being component (A).

The diacetal composition according to the present invention is not particularly limited and suitably selected, but examples of typical compositions are those composed of the following diacetal (component (A)), anionic surfactant (component (B)) and aliphatic monocarboxylic acid (component (C)).

A preferable diacetal composition is one in which
component (A) is at least one member selected from the group consisting of 1,3:2,4-O-dibenzylidene-D-sorbitol, 1,3:2,4-bis-O-(p-methylbenzylidene)-D-sorbitol, 1,3:2,4-bis-O-(p-ethylbenzylidene)-D-sorbitol, and 1,3:2,4-bis-O-(3,4-dimethylbenzylidene)-D-sorbitol;

component (B) is at least one member selected from the group consisting of lithium lauryl sulfate, sodium lauryl sulfate, potassium lauryl sulfate, lithium polyoxyethylene (the number of moles of ethylene oxide added=2 to 3 moles) lauryl ether sulfate, sodium polyoxyethylene (the number of moles of ethylene oxide added=2 to 3 moles) lauryl ether sulfate, and potassium polyoxyethylene (the number of moles of ethylene oxide added=2 to 3 moles) lauryl ether sulfate; and component (C) is at least one member selected from the group consisting of lauric acid, palmitic acid, myristic acid, stearic acid, 12-hydroxystearic acid and oleic acid.

The following combinations are preferable:
1,3:2,4-O-dibenzylidene-D-sorbitol+sodium lauryl sulfate+lauric acid,
1,3:2,4-O-dibenzylidene-D-sorbitol+sodium lauryl sulfate+stearic acid,
1,3:2,4-O-dibenzylidene-D-sorbitol+sodium lauryl sulfate+12-hydroxystearic acid,
1,3:2,4-bis-O-(p-methylbenzylidene)-D-sorbitol+sodium lauryl sulfate+lauric acid,
1,3:2,4-bis-O-(p-methylbenzylidene)-D-sorbitol+sodium lauryl sulfate+stearic acid,
1,3:2,4-bis-O-(p-methylbenzylidene)-D-sorbitol+sodium lauryl sulfate+12-hydroxystearic acid,
1,3:2,4-bis-O-(p-methylbenzylidene)-D-sorbitol+sodium polyoxyethylene (the number of moles of ethylene oxide added=3 moles) lauryl ether sulfate+lauric acid,
1,3:2,4-bis-O-(p-methylbenzylidene)-D-sorbitol+sodium polyoxyethylene (the number of moles of ethylene oxide added=3 moles) lauryl ether sulfate+stearic acid,
1,3:2,4-bis-O-(p-methylbenzylidene)-D-sorbitol+sodium polyoxyethylene (the number of moles of ethylene oxide added=3 moles) lauryl ether sulfate+12-hydroxystearic acid,
1,3:2,4-bis-O-(p-ethylbenzylidene)-D-sorbitol+sodium lauryl sulfate+lauric acid,
1,3:2,4-bis-O-(p-ethylbenzylidene)-D-sorbitol+sodium lauryl sulfate+stearic acid,
1,3:2,4-bis-O-(p-ethylbenzylidene)-D-sorbitol+sodium lauryl sulfate+12-hydroxystearic acid,
1,3:2,4-bis-O-(3,4-dimethylbenzylidene)-D-sorbitol+sodium lauryl sulfate+lauric acid,
1,3:2,4-bis-o-(3,4-dimethylbenzylidene)-D-sorbitol+sodium l auryl sulfate+stearic acid, and
1,3:2,4-bis-O-(3,4-dimethylbenzylidene)-D-sorbitol+sodium lauryl sulfate+12-hydroxystearic acid.

Of these, the following are recommended as more effective compositions:
1,3:2,4-O-dibenzylidene-D-sorbitol+sodium lauryl sulfate+stearic acid,
1,3:2,4-bis-O-(p-methylbenzylidene)-D-sorbitol+sodium lauryl sulfate+stearic acid, 1,3:2,4-bis-O-(p-methylbenzylidene)-D-sorbitol+sodium polyoxyethylene (the number of moles of ethylene oxide added=3 moles) lauryl ether sulfate+stearic acid, 1,3:2,4-bis-O-(p-methylbenzylidene)-D-sorbitol+sodium lauryl sulfate+12-hydroxystearic acid, and 1,3:2,4-bis-O-(3,4-dimethylbenzylidene)-D-sorbitol+ sodium lauryl sulfate+stearic acid.

Method for Manufacturing the Diacetal Composition of the Present Invention

As long as the desired diacetal composition can be obtained, there are no particular restrictions on the manufacturing method for obtaining the composition according to the present invention, in which an anionic surfactant (component (B)) and an aliphatic monocarboxylic acid (component (C)) are uniformly dispersed in diacetal particles.

There are no particular restrictions on the form or average particle diameter of the raw material diacetal represented by the formula (1), but it is usually preferable to use the diacetal in the form of a readily available powder.

In the course of manufacturing the diacetal composition of the present invention, the raw material diacetal is in a swollen or dissolved state by the action of a solvent, and therefore the form and average particle diameter of the raw material diacetal seldom adversely affect the invention of the diacetal composition according to the present invention. Still, a raw material diacetal that is in the form of a powder or has a smaller average particle diameter can be made into a swollen or dissolved state within a shorter time, and thus contributes to productivity improvement and cost reduction.

According to an example of a method for manufacturing the diacetal composition according to the present invention, when diacetal crystals are thoroughly swollen with a solvent or dissolved in a solvent, the specified anionic surfactant and the specified aliphatic monocarboxylic acid (which may be in the form of a melt or a solution) are added, and the resulting mixture is dried (to remove the solvent or water), and the volatile component content of the diacetal composition is adjusted to 1 wt % or less. The resulting dry product is then pulverized or crushed, or is granulated, classified, and so forth.

The important points of this manufacturing method are summarized below.

1) A low-boiling solvent is used.

The boiling point (at normal pressure) of the solvent is 150° C. or lower, preferably 120° C. or lower, more preferably 100° C. or lower. More specifically, this solvent can be methanol, ethanol, isopropanol or like lower alcohols, tetrahydrofuran, dioxane or like ether compounds, acetone, MEK or like ketone compounds, or the like. The above solvents can also be used in combination with water, if so desired. A high-boiling solvent, when used, tends to remain in the diacetal composition, and therefore tends to deteriorate storage stability of the diacetal.

2) The volatile component content of the diacetal composition after drying is adjusted to 1 wt % or less, preferably 0.5 wt % or less, more preferably 0.3 wt % or less.

If the volatile component content is more than 1 wt %, storage stability tends to be inferior, and void formation and so forth sometimes occur when the composition is made into a polyolefin resin composition and molded products, and the appearance and/or transparency may be impaired. As long as the conditions of 2) are satisfied, there are no particular restrictions on the drying conditions, but sometimes the diacetal composition itself undergoes coloration depending on the drying time and drying temperature. It is recommended that the drying be carried out under reduced pressure and at a temperature of, for example, 120° C. or lower, preferably 100° C. or lower, more preferably 80° C. or lower.

The diacetal composition of the present invention may take any form as suitably selected, and may be in the form of a usual powder or grains, or in a granulated form such as granules, cylinders, pellets and the like.

In the case of a powder, the average particle diameter thereof is 3 to 2000 $\mu$m, preferably 7 to 250 $\mu$m. If the average particle diameter is smaller than 3 $\mu$m, powder characteristics tends to be poor, and a special pulverization apparatus is necessary.

In the case of granules, a granular diacetal composition of the desired shape and size can be obtained from a powdery diacetal composition obtained by the above method. This granular diacetal composition is advantageous in that it has reduced dust generation and improved particle fluidity, as compared with a powdery diacetal composition.

Any of the above forms can be manufactured using a known granulator, pulverizer/crusher, classifier, or the like. Examples of granulators include dry or wet extrusion granulators, mixing and stirring granulators, tableting machines, dry compression roll granulators, and oscillating granulator. Examples of pulverizer/crushers include pin mills, jet mills, pulverizers, cutter mills, hammer mills, planar crushers, flake crushers, nibblers, etc. Examples of classifiers include vibrating sifters, air classifiers, etc.

The diacetal composition of the present invention obtained as above produces the effect of having a melting point much depressed relative to the melting point of the diacetal itself, without using a dicarboxylic acid such as L-tartaric acid, succinic acid, citric acid or DL-malic acid disclosed in the examples of WO99/18108, and also has better storage stability than the above-mentioned dicarboxylic acid-containing diacetal composition.

The use of the diacetal composition of the present invention achieves the following advantages.

(1) The diacetal composition, in which the above-mentioned specific compounds are uniformly dispersed in diacetal powder particles, has much more improved solubility and dispersibility in molten resin and various liquids, and much more improved dissolution rate.

(2) Said composition, even when provided in a granulated form such as pellets or granules, has good solubility and dispersibility in molten resin and various liquids. Furthermore, the use of such granulated product results in better powder characteristics, such as better dust fluidity, reduced dust generation, suppression of dust explosion, and suppression of adhesion to the walls inside feed hoppers.

(3) Storage stability, particularly storage stability when the composition is stored at high temperature, is remarkably improved.

(4) Because the diacetal can be dissolved at a considerably low temperature, the diacetal does not decompose or sublime during processing. Furthermore, processing at a lower temperature results in energy saving.

(5) A sufficient melting point depression action is exhibited even when the melting point depressants, i.e., above-mentioned components (B) and (C), are used in a small combined amount, so that the nucleating agent effect of the diacetal is unlikely to be relatively reduced when used within a practical range.

Polyolefin Resin Nucleating Agent

The diacetal composition used for the polyolefin resin nucleating agent of the present invention is useful as a polyolefin resin nucleating agent, and has a markedly lower melting point than the diacetal itself and excellent dispersibility because an anionic surfactant (component (B)) and an aliphatic monocarboxylic acid (component (C)) are used together and uniformly dispersed in the diacetal particles.

When the diacetal composition of the present invention having these characteristics is used as a nucleating agent, the rate of dissolution in molten polyolefin resins increases, and solubility and dispersibility are improved, and the following advantages are given.

(a) Processing can be carried out at a lower temperature than conventional processing temperature (220 to 260° C. in the case of polypropylene resins). In particular, with the present invention, processing can be carried out at a temperature which is lower than the melting point of the diacetal composition of the present invention, and even when such low temperature processing is performed, the dispersibility of the nucleating agent is good. Because low temperature processing is possible, sublimation of the diacetal is reduced, and therefore there is less mold fouling and so forth during molding. Yellowing of the polyolefin resin molding is also reduced.

(b) Productivity and product quality are improved because of the dramatic reduction in undispersed matter in the polyolefin resin composition and moldings thereof.

(c) It is much easier to prepare high-concentration master batch pellets composed of this diacetal composition and a polyolefin resin.

(d) When used at conventional processing temperatures, the diacetal composition dissolves and melts faster, so that the heating residence time during kneading is much shortened.

As a result, productivity is greatly enhanced, and energy costs and so on can be reduced.

(e) A polyolefin resin molding with an excellent appearance and good transparency is obtained.

(f) Because the specified anionic surfactant and the specified aliphatic monocarboxylic acid are contained in small quantities in the diacetal composition, the amount of the diacetal composition to be added to a resin can be substantially the same as the conventional amount of the diacetals represented by the formula (1) above.

The nucleating agent of the present invention is generally composed of only the above-mentioned diacetal composition of the present invention, but to the extent that the melting point depression of the present invention is not hindered, a conventional polyolefin modifier can be added as needed, as long as the effect of the present invention is not compromised.

Examples of such polyolefin modifiers include the various additives listed in "The Tables of Positive Lists of Additives" edited by the Japan Hygienic Olefin and Styrene Plastic Association (January, 1995). More specific examples include stabilizers (such as metal compounds, epoxy compounds, nitrogen compounds, phosphorus compounds, and sulfur compounds), UV absorbers (such as benzophenone compounds and benzotriazole compounds), antioxidants (such as phenol compounds, phosphorous ester compounds, and sulfur compounds), surfactants, lubricants (such as paraffin, wax, and other aliphatic hydrocarbons, $C_8$ to $C_{22}$ higher fatty acids, $C_8$ to $C_{22}$ higher fatty acid metal (Al, Ca, Mg, Zn) salts, $C_8$ to $C_{22}$ higher fatty acid aliphatic alcohols, polyglycols, esters of $C_4$ to $C_{22}$ higher fatty acids and $C_4$ to $C_{18}$ aliphatic monohydric alcohols, $C_8$ to $C_{22}$ higher fatty acid amides, silicone oils, and rosin derivatives), fillers (such as talc, hydrotalcite, mica, zeolite, perlite, diatomaceous earth, calcium carbonate, and glass fibers), foaming agents, foaming auxiliaries, polymer additives, plasticizers (such as dialkyl phthalates and dialkyl hexahydrophthalates), crosslinking agents, crosslinking accelerators, antistatic agents, flame retardants, dispersants, organic and inorganic pigments, working auxiliaries, other nucleating agents, and like additives.

When these other components are added, one method that may be employed is to dry blend the diacetal composition of the present invention with these other components to obtain a uniform mixture.

Polyolefin Resin Composition

The polyolefin resin composition according to the present invention is obtained by incorporating the polyolefin resin nucleating agent of the present invention into a polyolefin resin by a standard method.

Compared to a polyolefin resin composition obtained by known techniques, the polyolefin resin composition of the present invention contains far less diacetal that remains undispersed or undissolved during processing, and therefore has excellent performance such that the final product has good transparency and a superior appearance that is free from fisheyes, white spots and the like attributable to undispersed diacetal.

The polyolefin resin composition of the present invention can be manufactured by any conventional method, with no particular restrictions thereon, as long as the desired resin composition is obtained.

For example, a polyolefin resin (powder or flakes), the polyolefin resin nucleating agent of the present invention, and, if needed, a polyolefin modifier discussed below are mixed in a conventional mixer, such as Henschel mixer, V-blender or ribbon blender, to obtain a blend type of polyolefin resin composition. Other examples include a method in which this blend type of polyolefin resin composition is melt kneaded at the desired temperature in a conventional kneader, such as a single screw or twin screw extruder, the extruded strands are cooled, and the strands thus obtained are cut into pellets, as well as a method that is a variation of this pellet type, in which master batch pellets are made from a polyolefin resin nucleating agent and a polyolefin resin.

However, because a nucleating agent composed of the diacetal composition of the present invention has a good melting point depression effect as mentioned above, so that the temperature can be lowered in the manufacture of pellets by incorporating the diacetal composition of the present invention into a polyolefin resin. For example, a polyolefin resin composition in the form of pellets can be easily manufactured by melting a mixture containing the diacetal composition (nucleating agent) of the present invention and a polyolefin resin at a temperature which is not lower than the melting point of the polyolefin resin (in particular 160° C. or higher, preferably 180° C. or higher) and not higher than the melting point of the diacetal composition, and pelletizing the melt thus obtained.

There are no particular restrictions on the amount of the polyolefin resin nucleating agent according to the present invention to be added, as long as the desired diacetal nucleating agent effect is obtained, and this amount can be suitably selected. Usually, the amount is 0.01 to 5 weight parts, preferably 0.05 to 3 weight parts, per 100 weight parts of the polyolefin resin. Blending within this range produces the desired diacetal nucleating agent effect. When the resin composition is in the form of master batch pellets composed of said nucleating agent and a polyolefin resin, the nucleating agent is blended in an amount of 2 to 20 weight parts, preferably 5 to 15 weight parts, per 100 weight parts of the polyolefin resin, and the nucleating agent can be adjusted to the specified amount by diluting with a polyolefin resin.

The polyolefin resin according to the present invention is a crystalline resin having a crystallinity of 5 to 100%, preferably 15 to 95%. Specific examples include polyethylene-based resins, stereoregular polypropylene-based resins, stereoregular polybutene-based resins, stereoregular ethylene-propylene-butadiene and like terpolymer resins, methylpentene-based resins, and polybutadiene.

Examples of polyethylene-based resins include high-density polyethylene, medium-density polyethylene, low-density polyethylene, linear low-density polyethylene, and ethylene copolymers with an ethylene content of at least 50 wt %, and especially 70 wt % or higher.

Examples of polypropylene-based resins include propylene homopolymers, and propylene copolymers with a propylene content of at least 50 wt %, and especially 70 wt % or higher.

Examples of polybutene-based resins include butene homopolymers, and butene copolymers with a butene content of at least 50 wt %, and especially 70 wt % or higher.

Examples of methylpentene-based resins include methylpentene homopolymers, and methylpentene copolymers with a methylpentene content of at least 50 wt %, and especially 70 wt % or higher.

The above copolymers may be random copolymers or block copolymers. The stereoregularity of these resins may be either isotactic or syndiotactic.

Specific examples of comonomers which can form the various copolymers above include ethylene, propylene, butene, pentene, hexene, heptene, octene, nonene, decene, undecene, dodecene and like α-olefins (especially $C_2$ to $C_{12}$ α-olefins); 1,4-endomethylenecyclohexene and like bicyclo-type monomers; methyl (meth)acrylate, ethyl (meth)acrylate, and like (meth)acrylic esters; vinyl acetate; and maleic acid.

Any known catalyst can be used in the manufacture of these polymers, with no restrictions thereon. Catalysts that can be used include not only radical polymerization catalysts and Ziegler-Natta catalysts which are commonly used, but also a catalyst system comprising a combination of a transition metal compound (e.g., a titanium halide such as titanium trichloride or titanium tetrachloride) supported on a support comprising as a main component magnesium chloride or like magnesium halide, with an alkyl aluminum compound (such as triethyl aluminum or diethyl aluminum chloride), and metallocene catalysts.

The recommended melt flow rate (hereinafter referred to as "MFR", measured according to JIS K 7210-1976) of the polyolefin resin according to the present invention can be suitably selected according to the molding method to be employed and the physical properties required of the molded article, but is usually 0.01 to 200 g/10 minutes, preferably 0.05 to 100 g/10 minutes. Use of a mixture of different kinds of polyolefin resins or resins with different MFR values is also recommended, as long as the MFR is within the above specified range.

To the extent that the effect of the present invention is not lost, the above-mentioned known polyolefin modifiers can be added to the polyolefin resin composition of the present invention as dictated by the intended use and application thereof.

Polyolefin Resin Moldings

The polyolefin resin moldings of the present invention are obtained by molding the polyolefin resin composition of the present invention according to a conventional molding method.

In the polyolefin resin moldings of the present invention, there is a dramatic reduction in undispersed or undissolved diacetal during processing as compared to moldings produced by known techniques, and the final product therefore has a superior appearance that is free from fisheyes or white spots attributable to undispersed diacetal, and the resulting polyolefin resin moldings also have excellent transparency and so on. Furthermore, when the molded product is produced by a low temperature processing, there is also a marked improvement in respect of yellowing.

Any known method, such as injection molding, extrusion molding, blow molding, pressure forming, rotational molding, or film forming, can be employed as the method for molding the polyolefin resin composition according to the present invention. The processing conditions can be suitably selected from the wide range of conditions that have been employed in the past.

The polyolefin resin moldings of the present invention can be put to use in the same fields in which polyolefin resin compositions containing a conventional diacetal as a nucleating agent have been used.

Specific examples include medical instruments sterilized by heat, radiation or the like, such as disposable syringes, infusion and transfusion sets, equipment for collecting blood, etc.; packaging materials for foods, plants, etc. sterilized by radiation or the like; cases such as cases for clothes, containers for clothes, etc.; cups for heat-packaging foods, packaging containers for retort-processed foods; containers for use in microwave oven, containers for cans, vessels, etc. for beverages such as juice, tea, etc., cosmetics, medicines, shampoo, etc.; containers and caps for seasonings such as miso, soy sauce, etc.; cases and containers for foods such as water, rice, bread, pickles, etc.; sundries such as cases for use in refrigerators, etc.; stationeries; electric and mechanical parts; automobile parts, etc.

EXAMPLES

The present invention will now be described in detail with reference to examples and comparative examples, but the present invention is not limited to or by these examples.

The melting point and uniformity of the diacetal composition of the present invention, and the transparency (haze) of polyolefin resin moldings, dispersibility, and storage stability were measured and evaluated by the following methods.

Melting Point

This was measured using a differential scanning calorimeter (trade name "DSC-50") made by Shimadzu Corp. The temperature was raised at a rate of 10° C./minute, and the peak temperature attributable to diacetal was used as the melting point. The sample was used in an amount of 3 mg, and 3 mg of silica gel was used as a standard sample.

Uniformity (Check for Uniform Dispersion of Melting Point Depressant in Particles Prepared by Pulverization)

The powdery diacetal composition obtained by pulverization was visually inspected using a polarizing microscope under a crossed Nicol polarizer and analyzer at room temperature and elevated temperature. If the melting point depressant was uniformly dispersed in the particles of the powder, this was indicated by "○" while non-uniformly was indicated by "X".

Storage Stability of Diacetal Composition

The diacetal composition was left for two weeks in a 60° C. thermostatic tank, and the diacetal content in the composition was analyzed by gas chromatography. Using the diacetal content prior to heating as a reference, the weight ratio of the remaining diacetal was noted. The larger the value, the better the storage stability.

Haze Value (Improvement in Transparency)

The haze value of a polyolefin resin molding with a thickness of 1.0 mm was measured using a haze meter (made by Toyo Seki Seisakusho) according to JIS K 6714 and JIS K 6717. The smaller the measured value, the better the transparency.

Dispersibility (Dispersibility of the Diacetal Composition in Polyolefin Resin Molding)

The number of white spots caused by undispersed nucleating agent in ten polyolefin moldings (5 cm×5 cm×1.0 mm) was counted by visual inspection, and the average number per sheet was calculated. The smaller the number, the better the dispersibility.

Yellow Index

The yellow index of a polyolefin resin molding with a thickness of 2.0 mm was measured according to ASTM D1925 using a spectrophotometer (trade name "CM-3500d," made by Minolta). The smaller the measured value, the less the yellowing and the better the appearance.

The following methods were used to prepare the diacetal composition according to the present invention and to prepare and mold the polyolefin resin composition.

Method for Preparing Diacetal Composition

A diacetal (300 g), 500 g of methanol, and the anionic surfactant and aliphatic monocarboxylic acid listed for the various examples in Table 1 (used in amounts so as to achieve the weight ratios listed for the various examples in Table 1) were placed in a 5 L universal mixer (made by Dalton) equipped with a stirrer, a condenser having a decanter, a thermometer, a gas inlet and an oil bath.

After the air therein was replaced by nitrogen, the mixture was stirred under a nitrogen gas stream for 3 hours at a speed of 50 to 60 rpm and at an oil bath temperature setting of 70° C. (the system became a swelled paste form). Then, 100 g of distilled water was added, and the mixture was stirred for another one hour under the same condition.

The pressure was gradually reduced to remove the methanol and water from the system. After most of the methanol and water was removed, the oil bath temperature setting was raised to 100° C., and once the reduced pressure became 2.0 kPa or less, the system was dried with stirring for 5 hours. The end point of this drying was the point at which the volatile component content of the diacetal composition reached 1.0 wt % or less.

The volatile component content of the diacetal compositions in the examples and comparative examples obtained by this preparation method were all 0.3 wt % or less, as confirmed by determining the weight loss on heating.

The dry products thus obtained were pulverized in a small pulverizer to obtain powdery diacetal compositions.

Method for Preparing and Molding Polyolefin Resin Compositions

To 100 weight parts of an isotactic random polypropylene resin with an ethylene content of 3.0 wt % (MFR=20 g/10 minutes; hereinafter referred to as "r-PP") were added 0.25 weight part (calculated as pure diacetal) of the diacetal composition prepared above, 0.05 weight part of calcium stearate, and 0.05 weight part of tetrakis[methylene-3-(3,5-di-tert-butyl-4-hydroxyphenyl)propionato]methane (trade name "Irganox 1010", made by Ciba Specialty Chemicals), and these components were dry blended in a Henschel mixer. Then the mixture was melt kneaded and extruded using a single screw extruder (25 mm diameter, L/D=380 mm/20 mm, rotation=40 rpm) at a resin temperature of 220° C. The obtained strands were cooled with water and cut into pellets to obtain a polyolefin resin composition.

The polyolefin resin composition thus obtained was injection molded at a resin temperature of 220° C. and a molding temperature of 40° C. to prepare a polyolefin resin molding (test piece).

Example 1

A diacetal composition was prepared according to the method for preparing a diacetal composition given above, so as to achieve the weight ratios given in Table 1. The melting point and uniformity of the resulting diacetal composition were evaluated, and the evaluation results are given in Table 1.

Then, using the obtained diacetal composition, a polyolefin resin molding was obtained according to the above method for preparing and molding a polyolefin resin composition. The transparency, dispersibility, and yellow index of the obtained polyolefin resin molding were evaluated, and the evaluation results are shown in Table 1.

The abbreviations in Tables 1 to 3 and Table 5 are defined below.

"DBS": 1,3:2,4-O-dibenzylidene-D-sorbitol

"Me-DBS": 1,3:2,4-bis-O-(p-methylbenzylidene)-D-sorbitol

"3,4-DMDBS": 1,3:2,4-bis-o-(3,4-dimethylbenzylidene)-D-sorbitol

Examples 2 to 14

Diacetal compositions were prepared according to the method for preparing a diacetal composition given above, so as to achieve the weight ratios given in Table 1. The melting point and uniformity of the resulting diacetal compositions were evaluated, and the evaluation results are shown in Table 1.

Then, using the obtained diacetal compositions, polyolefin resin moldings were obtained according to the above method for preparing and molding a polyolefin resin composition, except that the 0.25 weight part calculated as pure diacetal was changed to 0.2 weight part. The transparency, dispersibility, and yellow index of the obtained polyolefin resin moldings were evaluated, and the evaluation results are shown in Table 1.

Comparative Examples 1 to 3

Comparative diacetal compositions were prepared according to the method for preparing a diacetal composition given above, so as to achieve the weight ratios given in Table 2.

The melting point and uniformity of the resulting comparative diacetal compositions were evaluated, and the evaluation results are shown in Table 2.

Then, using the obtained comparative diacetal compositions, comparative polyolefin resin moldings were obtained according to the above method for preparing and molding a polyolefin resin composition. The transparency, dispersibility, and yellow index of the obtained comparative polyolefin resin moldings were evaluated, and the evaluation results are shown in Table 2.

Comparative Examples 4 to 22

Comparative diacetal compositions were prepared according to the method for preparing a diacetal composition given above, so as to achieve the weight ratios given in Tables 2 and 3.

The melting point and uniformity of the resulting comparative diacetal compositions were evaluated, and the evaluation results are shown in Tables 2 and 3.

Next, using the obtained comparative diacetal compositions, comparative polyolefin resin moldings were obtained according to the above method for preparing and molding a polyolefin resin composition, except that the 0.25 weight part calculated as pure diacetal was changed to 0.2 weight part. The transparency, dispersibility, and yellow index of the obtained comparative polyolefin resin moldings were evaluated, and the evaluation results are shown in Tables 2 and 3.

TABLE 1

Examples 1–14 and 31 (Resin used: r-PP)

| Ex. | Diacetal | Anionic surfactant | Aliphatic monocarboxylic acid | m.p. (° C.) | Uniformity | Processing temp. (° C.) | Haze value (%) | Dispersibility (spot/sheet) | Yellow index |
|---|---|---|---|---|---|---|---|---|---|
| 1 | DBS 98.0 | sodium lauryl sulfate 1.0 | stearic acid 1.0 | 204 | ○ | 220 | 21 | 0 | 12.2 |
| 2 | Me—DBS 96.5 | sodium lauryl sulfate 1.0 | lauric acid 2.5 | 209 | ○ | 220 | 11 | 0 | 12.2 |
| 3 | Me—DBS 96.5 | sodium lauryl sulfate 1.0 | myristic acid 2.5 | 209 | ○ | 220 | 11 | 0 | 12.2 |
| 4 | Me—DBS 96.5 | sodium lauryl sulfate 1.0 | palmitic acid 2.5 | 208 | ○ | 220 | 11 | 0 | 12.1 |
| 5 | Me—DBS 96.5 | sodium lauryl sulfate 1.0 | stearic acid 2.5 | 208 | ○ | 220 | 11 | 0 | 12.1 |
| 6 | Me—DBS 96.5 | sodium lauryl sulfate 1.0 | 12-hydroxystearic acid 3.0 | 208 | ○ | 220 | 11 | 0 | 12.2 |
| 7 | Me—DBS 96.5 | potassium lauryl sulfate 1.0 | oleic acid 3.0 | 209 | ○ | 220 | 11 | 0 | 12.2 |
| 8 | Me—DBS 96.5 | lithium lauryl sulfate 1.0 | stearic acid 2.5 | 207 | ○ | 220 | 11 | 0 | 12.2 |
| 9 | Me—DBS 97.5 | ammonium lauryl sulfate 1.0 | lauric acid 1.5 | 190 | ○ | 220 | 11 | 0 | 12.7 |
| 10 | Me—DBS 96.5 | sodium polyoxyethylene (3 moles added) lauryl ether sulfate 1.0 | stearic acid 2.5 | 211 | ○ | 220 | 11 | 0 | 12.3 |
| 11 | Me—DBS 96.5 | sodium monolauric acid glyceryl sulfate 1.0 | lauric acid 2.5 | 213 | ○ | 220 | 11 | 0 | 12.1 |
| 12 | Me—DBS 96.5 | sodium lauryl sulfate 2.0 | lauric acid 1.5 | 200 | ○ | 220 | 12 | 0 | 12.3 |
| 13 | 3,4-DMDBS 96.5 | sodium lauryl sulfate 1.0 | stearic acid 2.5 | 218 | ○ | 220 | 12 | 0 | 12.2 |
| 14 | 3,4-DMDBS 96.5 | potassium oleyl sulfate 1.0 | stearic acid 2.5 | 220 | ○ | 220 | 12 | 0 | 12.2 |
| 31 | Me—DBS 96.5 | sodium lauryl sulfate 1.0 | stearic acid 2.5 | 208 | ○ | 220 | 11 | 0.4 | 12.2 |

TABLE 2

Comparative Examples 1–11 (Resin used: r-PP)

| Comp. Ex. | Diacetal | Anionic surfactant | Aliphatic monocarboxylic acid | m.p. (° C.) | Uniformity | Processing temp. (° C.) | Haze value (%) | Dispersibility (spot/sheet) | Yellow Index |
|---|---|---|---|---|---|---|---|---|---|
| 1 | DBS 100 | — | — | 226 | — | 220 | 21 | 1.0 | 12.2 |
| 2 | DBS 99.0 | sodium lauryl sulfate 1.0 | — | 211 | ○ | 220 | 21 | 0.3 | 12.2 |
| 3 | DBS 99.0 | — | stearic acid 1.0 | 224 | ○ | 220 | 21 | 0.9 | 12.2 |
| 4 | Me—DBS 100 | — | — | 262 | — | 220 | 12 | 8.0 | 12.2 |
| 5 | Me—DBS 99.0 | sodium lauryl sulfate 1.0 | — | 222 | ○ | 220 | 11 | 0.6 | 12.2 |
| 6 | Me—DBS 98.0 | sodium lauryl sulfate 2.0 | — | 212 | ○ | 220 | 12 | 0.3 | 12.3 |
| 7 | Me—DBS 99.0 | potassium lauryl sulfate 1.0 | — | 223 | ○ | 220 | 11 | 0.5 | 12.3 |
| 8 | Me—DBS 99.0 | lithium lauryl sulfate 1.0 | — | 221 | ○ | 220 | 11 | 0.5 | 12.3 |
| 9 | Me—DBS 99.0 | Ammonium lauryl sulfate 1.0 | — | 198 | ○ | 220 | 12 | 0.1 | 12.7 |
| 10 | Me—DBS 99.0 | sodium polyoxyethylene (3 moles added) lauryl ether sulfate 1.0 | — | 225 | ○ | 220 | 11 | 0.7 | 12.4 |
| 11 | Me—DBS 99.0 | sodium monolauric acid glyceryl sulfate 1.0 | — | 226 | ○ | 220 | 11 | 0.7 | 12.2 |

TABLE 3

Comparative Examples 12–22 (Resin used: r-PP)

| Comp. Ex. | Diacetal | Anionic surfactant | Aliphatic monocarboxylic acid | m.p. (° C.) | Uniformity | Processing temp. (° C.) | Haze value (%) | Dispersibility (spot/sheet) | Yellow Index |
|---|---|---|---|---|---|---|---|---|---|
| 12 | Me—DBS 98.5 | — | lauric acid 1.5 | 256 | ○ | 220 | 12 | 7.2 | 12.2 |
| 13 | Me—DBS 97.5 | — | lauric acid 2.5 | 255 | ○ | 220 | 12 | 7.0 | 12.3 |

TABLE 3-continued

Comparative Examples 12–22 (Resin used; r-PP)

| Comp. Ex. | Diacetal | Anionic surfactant | Aliphatic monocarboxylic acid | m.p. (° C.) | Uniformity | Processing temp. (° C.) | Haze value (%) | Dispersibility (spot/sheet) | Yellow Index |
|---|---|---|---|---|---|---|---|---|---|
| 14 | Me—DBS 97.5 | — | myristic acid 2.5 | 255 | ○ | 220 | 12 | 6.7 | 12.3 |
| 15 | Me—DBS 97.5 | — | palmitic acid 2.5 | 254 | ○ | 220 | 12 | 6.5 | 12.3 |
| 16 | Me—DBS 97.5 | — | stearic acid 2.5 | 254 | ○ | 220 | 12 | 6.4 | 12.3 |
| 17 | Me—DBS 97.0 | — | 12-hydroxystearic acid 3.0 | 253 | ○ | 220 | 12 | 6.2 | 12.3 |
| 18 | Me—DBS 97.0 | — | oleic acid 3.0 | 254 | ○ | 220 | 12 | 6.2 | 12.4 |
| 19 | 3,4-DMDBS 100 | — | — | 275 | — | 220 | 13 | 9.9 | 12.4 |
| 20 | 3,4-DMDBS 99.0 | sodium lauryl sulfate 1.0 | — | 230 | ○ | 220 | 12 | 1.0 | 12.3 |
| 21 | 3,4-DMDBS 99.0 | potassium oleyl sulfate 1.0 | — | 231 | ○ | 220 | 12 | 1.1 | 12.4 |
| 22 | 3,4-DMDBS 97.5 | — | stearic acid 2.5 | 267 | ○ | 220 | 13 | 8.0 | 12.3 |

The following points are clear from Tables 1 to 3 above.

1) Melting Point Depression Effect

As clear from Tables 1 to 3, the combined use of an anionic surfactant (component (B)) and an aliphatic monocarboxylic acid (component (C)) depresses the melting point more than when either of these is used alone. Even assuming that there is an additivity in this melting point depression, the resulting melting point depression is greater than the depression expected from the additivity, and therefore this phenomenon is considered quite distinctive.

2) Dispersibility Promotion Effect

Comparison of Example 5 and Comparative Example 6, for instance, reveals that there is a significant difference in the dispersibility in the polyolefin resin moldings, despite the fact that they were processed at a resin temperature which was not lower than the melting point. This significant difference is even more pronounced in low temperature processing and processing on a commercial scale. This phenomenon indicates that when diacetal compositions have a similar melting point, the diacetal composition prepared by the combined use of the two components is more excellent in dispersibility than the diacetal composition prepared by using one of these components.

3) Proportion of Anionic Surfactant (Component (B))

The greater the weight ratio of component (B) is, the more the melting point tends to decrease. On the other hand, a higher weight ratio of component (B) also tends to diminish the transparency of the polyolefin resin.

Specifically, the lower limit to the amount of component (B) tends to be controlled by the melting point depression effect, while the upper limit tends to be controlled by the polyolefin resin modifying effect.

Examples 15 to 25

The low temperature processing characteristics of the diacetal compositions of the present invention were tested. Specifically, polyolefin resin moldings were produced using the diacetal compositions obtained in Examples 1 to 8 and 10 to 12 and following the procedure of the above method for preparing and molding a polyolefin resin composition, except that the kneaded resin temperature was set at 200° C., and the injection molding temperature was set at 200° C., which temperatures were not higher than the melting point of the diacetal composition. The transparency, dispersibility, and yellow index of the polyolefin resin moldings thus obtained were evaluated, and the evaluation results are shown in Table 4.

Comparative Examples 23 to 29

Comparative polyolefin resin moldings were produced using the comparative diacetal compositions obtained in Comparative Examples 2, 5 to 8, and 10 and 11 and following the procedure of the above method for preparing and molding a polyolefin resin composition, except that the kneaded resin temperature was set at 200° C., and the injection molding temperature was set at 200° C., which temperatures were not higher than the melting point of the comparative diacetal composition. The transparency, dispersibility, and yellow index of the comparative polyolefin resin moldings thus obtained were evaluated, and the results are given in Table 4.

TABLE 4

Examples 15–25 and Comparative Examples 23–29 (low temperature processing characteristics)

| | Diacetal composition used | m.p. (° C.) | Processing temp. (° C.) | Haze value (%) | Dispersibility (spot/sheet) | Yellow Index |
|---|---|---|---|---|---|---|
| Ex. | | | | | | |
| 15 | Example 1 | 204 | 200 | 21 | 0.1 | 11.3 |
| 16 | Example 2 | 209 | 200 | 11 | 0.1 | 11.2 |
| 17 | Example 3 | 209 | 200 | 11 | 0.1 | 11.2 |
| 18 | Example 4 | 208 | 200 | 11 | 0.1 | 11.1 |
| 19 | Example 5 | 208 | 200 | 11 | 0.1 | 11.1 |
| 20 | Example 6 | 208 | 200 | 11 | 0.1 | 11.1 |
| 21 | Example 7 | 209 | 200 | 11 | 0.1 | 11.2 |
| 22 | Example 8 | 207 | 200 | 11 | 0.1 | 11.2 |
| 23 | Example 10 | 211 | 200 | 11 | 0.2 | 11.2 |
| 24 | Example 11 | 213 | 200 | 11 | 0.2 | 11.2 |
| 25 | Example 12 | 200 | 200 | 12 | 0 | 11.2 |
| Comp. Ex. | Comparative diacetal composition used | | | | | |
| 23 | Comparative Example 2 | 211 | 200 | 22 | 0.9 | 11.2 |
| 24 | Comparative Example 5 | 222 | 200 | 12 | 1.4 | 11.2 |
| 25 | Comparative Example 6 | 212 | 200 | 12 | 0.9 | 11.3 |
| 26 | Comparative Example 7 | 223 | 200 | 12 | 1.5 | 11.2 |

TABLE 4-continued

Examples 15–25 and Comparative Examples 23–29
(low temperature processing characteristics)

|  | Diacetal composition used | m.p. (° C.) | Processing temp. (° C.) | Haze value (%) | Dispersibility (spot/sheet) | Yellow Index |
|---|---|---|---|---|---|---|
| 27 | Comparative Example 8 | 221 | 200 | 12 | 1.3 | 11.2 |
| 28 | Comparative Example 10 | 225 | 200 | 12 | 1.5 | 11.3 |
| 29 | Comparative Example 11 | 226 | 200 | 12 | 1.7 | 11.2 |

As is clear from Table 4, the diacetal compositions of the present invention maintained a practical level of dispersibility even at a low processing temperature of 200° C., which is lower than the conventional processing temperature (220 to 260° C.), and is also improved in respect of yellowing. On the other hand, with the comparative diacetal compositions, the dispersibility was not really adequate at the above-mentioned low temperature molding at 200° C.

Example 26

Storage stability was evaluated using the diacetal compositions obtained in Examples 1 to 14 and 31, and the evaluation results are given in Table 5. There was no decrease in diacetal content in any of these diacetal compositions.

For the sake of reference, data for the melting point and uniformity of the diacetal compositions obtained in Examples 1 to 14 and 31 (shown in Table 1) are also shown in Table 5.

Comparative Examples 30 and 31

Comparative diacetal compositions were obtained according to the above method for preparing and molding a polyolefin resin composition, so as to achieve the weight ratios given in Table 5. The melting point, uniformity, and storage stability of the resulting comparative diacetal compositions were evaluated, and the evaluation results are given in Table 5.

TABLE 5

Example 26 and Comparative Examples 30 and 31
(storage stability)

| Ex. | Diacetal composition used | | m.p. (° C.) | Uniformity | storage stability (%) |
|---|---|---|---|---|---|
| 26 | Examples 1–14 and 31 | | 190 to 220 | ○ | 100 |

| | Comparative diacetal composition/ weight ratio (wt. %) | | | | |
|---|---|---|---|---|---|
| Comp. Ex. | Diacetal | Aliphatic monocarboxylic acid | | | |
| 30 | Me—DBS 99.6 | L-tartaric acid 0.4 | 197 | ○ | 89 |
| 31 | Me—DBS 97.0 | DL-malic acid 3.0 | 201 | ○ | 86 |

As is clear from Table 5, the melting point was lowered considerably with L-tartaric acid or DL-malic acid, but when the compositions were stored for two weeks at 60° C., the diacetal content decreased approximately 10%. In contrast, the diacetal compositions of the present invention maintained the same diacetal content they had immediately after being prepared, and therefore had superior storage stability.

Example 27

The procedure of Example 5 was repeated except that an isotactic homopolypropylene resin (MFR=30 g/10 minutes, hereinafter referred to as "h-PP") was used instead of the r-PP. The evaluation results are given in Table 6.

Example 28

The procedure of Example 12 was repeated except that a linear low density polyethylene resin (MFR=20 g/10 minutes, hereinafter referred to as "LLDPE") was used instead of the r-PP and that the kneaded resin temperature and the injection molding temperature were both changed to 200° C. The evaluation results are given in Table 6.

Comparative Example 32

The procedure of Comparative Example 5 was repeated except that h-PP was used instead of r-PP. The evaluation results are given in Table 6.

Comparative Example 33

The procedure of Comparative Example 6 was repeated except that the kneaded resin temperature and the injection molding temperature were both changed to 200° C. The evaluation results are given in Table 6.

TABLE 6

Examples 27, 28 and Comparative Examples 32, 33
(examples of application to h-PP and LLDPE)

| | Diacetal composition used | m.p. (° C.) | Resin | Processing temp. (° C.) | Haze value (%) | Dispersibility (spot/sheet) | Yellow Index |
|---|---|---|---|---|---|---|---|
| Ex. | | | | | | | |
| 27 | Example 5 | 208 | h-PP | 220 | 23 | 0 | 12.7 |
| 28 | Example 12 | 200 | LLDPE | 200 | 31 | 0.1 | 10.8 |
| Comp. Ex. | | | | | | | |
| 32 | Comparative Example 5 | 222 | h-PP | 220 | 24 | 0.7 | 12.9 |
| 33 | Comparative Example 6 | 212 | LLDPE | 200 | 32 | 1.1 | 10.9 |

As is clear from Table 6, the diacetal compositions of the present invention can be applied to other polyolefin resins besides r-PP, such as h-PP or LLDPE, and the improvement in dispersibility and so forth when applied to r-PP is achieved in the other resins as well.

Comparative Example 34

A comparative resin molding was produced following the above method for preparing and molding a polyolefin resin composition except that the diacetal composition of the present invention was not used. The evaluation results are given in Table 7.

Comparative Example 35

A comparative resin molding was produced following the above method for preparing and molding a polyolefin resin composition except that the diacetal composition of the present invention was not used and that h-PP was used instead of r-PP. The evaluation results are given in Table 7.

Comparative Example 36

A comparative resin molding was produced following the above method for preparing and molding a polyolefin resin composition with the exception of not using the diacetal composition of the present invention and using LLDPE instead of r-PP and changing the kneaded resin temperature and injection molding temperature to 200° C. The evaluation results are given in Table 7.

Comparative Example 37

A comparative resin molding was produced following the above method for preparing and molding a polyolefin resin composition with the exception of not using the diacetal composition of the present invention and changing the kneaded resin temperature and injection molding temperature to 200° C. The evaluation results are given in Table 7.

TABLE 7

Comparative Examples 34–37
(evaluation of molding of resin alone)

| Comp. Ex. | Resin | Processing temp. (° C.) | Haze value (%) | Yellow Index |
|---|---|---|---|---|
| 34 | r-PP | 220 | 70 | 12.9 |
| 35 | h-PP | 220 | 78 | 12.9 |
| 36 | LLDPE | 200 | 55 | 10.9 |
| 37 | r-PP | 200 | 71 | 11.5 |

As is clear from Table 7, when the diacetal composition of the present invention was not used, transparency was extremely low, as seen from the high haze value of the resin moldings prepared at molding temperatures of 220° C. and 200° C. In contrast, as can be seen from Table 1 and the like, there was a marked improvement in respect of haze when the diacetal composition of the present invention was used.

As to yellow index, the diacetal composition, when used as a polyolefin resin nucleating agent, has no adverse effect on the yellowing of the polyolefin resin itself, and therefore the diacetal composition of the present invention can be used in a conventional manner.

Example 29 and Comparative Example 38

A diacetal composition (Example 29) and a comparative diacetal composition (Comparative Example 38) were prepared following the above method for preparing and molding a polyolefin resin composition, so as to achieve the weight ratios shown in FIG. 1. FIG. 1 also shows the results of the melting point measurement.

FIG. 1 shows the influence of the weight ratio (X wt %) of sodium lauryl sulfate on the effect of depressing the melting point of the diacetal and on the effect of combined use with stearic acid, when the amount of stearic acid is fixed at 2.0 wt %.

Specifically, the composition of Example 29 is such that Me-DBS:sodium lauryl sulfate:stearic acid=(98.0−X):X:2.0, and the composition of Comparative Example 38 is such that Me-DBS:sodium lauryl sulfate=(100−X):X.

FIG. 1 reveals the following:

1) When sodium lauryl sulfate is used alone, it is difficult to lower the melting point of the diacetal composition below 200° C., and the amount thereof to be used must be increased to more than 5 wt %. The use of sodium lauryl sulfate in such a large amount tends to result in a polyolefin resin having impaired transparency. When the amount is over 3 wt %, it may be impossible to use the composition in applications in which conventional polyolefin resin moldings have been used.

In contrast, when sodium lauryl sulfate is used together with stearic acid according to the present invention, the melting point of the diacetal composition becomes under 200° C. when the amount of sodium lauryl sulfate used is only about 2 wt %.

2) By the combined use of sodium lauryl sulfate and stearic acid, the melting point of the diacetal is lowered even below the melting point predicted based on the assumed additivity.

Usually there is a linear relation over a certain range between melting point depression and the added amount (moles) based on the theory of freezing point depression. Nevertheless, component (B) or component (C), even when used alone, exhibits melting point depression behavior that cannot be explained by the theory of freezing point depression, and when component (B) and component (C) are used together as in the present invention, the range of processing resin temperatures can be extended downward because of the effect of increasing dispersibility and further depressing the melting point of the diacetal.

3) As to the amount of sodium lauryl sulfate in Example 29, the lower limit of the amount to be used is 0.1 wt %, since the melting point depression effect is produced when sodium lauryl sulfate is used in an amount of at least 0.1 wt %. If we take into account the applications in which polyolefin resin moldings have heretofore been used (and particularly the transparency of the polyolefin resin), the upper limit of its amount should be 3 wt %.

As seen from FIG. 1, in order to obtain stable performance and quality when the diacetal composition is commercially manufactured, recommended amount is in the range of 0.5 to 2 wt %, in which the curve in the graph shows a gentle slope.

Example 30

A diacetal composition was prepared following the above method for preparing and molding a polyolefin resin composition, so as to achieve the weight ratios shown in FIG. 2. FIG. 2 also shows the results of the melting point measurement.

FIG. 2 shows the influence of the weight ratio (Y wt %) of stearic acid on the melting point depression and on the effect of combined use with sodium lauryl sulfate, when the amount of sodium lauryl sulfate is fixed at 1.0 wt %. The composition of Example 30 is such that Me-DBS:sodium lauryl sulfate:stearic acid=(99.0−Y):1.0:Y.

FIG. 2 reveals the following:

1) When stearic acid is used together with sodium lauryl sulfate, there is a pronounced decrease in the melting point of the diacetal composition.

2) A melting point depression effect and combined use effect are produced when stearic acid is used in Example 30 in an amount of at least 0.3 wt %. The upper limit of the amount to be used is 5 wt % for the sake of the nucleating agent effect of the polyolefin resin, the melting point depression effect, and the dispersibility promotion effect.

In order to obtain stable performance and quality when the diacetal composition is commercially manufactured, a range of 1 to 3 wt % is recommended in which the curve in the graph of FIG. 2 shows a gentle slope.

3) The combined use effect of stearic acid (component (C)) and sodium lauryl sulfate (component (B); 1.0 wt %) in Example 30 is realized at a ratio of component (B): component (C)=1:0.3 or higher, and the improvement in the combined use effect is saturated when the ratio of component (B): component (C) is 1:4 or higher. Specifically, from the standpoint of the combined use effect, the recommended weight ratio of component (B): component (C) is 1:0.3 to 4, especially 1:0.5 to 3.

Example 31

The powdery diacetal composition of Example 5 was compressed using a dry compression roll granulator into a plate with a width of 25 cm at a roll pressure of 5 MPa. Then, using a hammer mill, the compressed sheet was crushed at a speed of 1000 rpm with a screen mesh having an opening dimension of 1 mm.

The diacetal composition particles thus obtained had an average particle diameter of 200 μm. A dry particle size measurement apparatus (trade name: Microtrac MT3300 (high-speed multi-point processing model, Super Dry X), manufactured by Microtrac) was used to measure the particle size distribution.

Table 1 shows the results of evaluating the melting point and uniformity of the diacetal composition particles thus obtained.

In the above method for producing particles, the particle size distribution can be adjusted as desired by varying the compression pressure, rotation speed during pulverization, screen mesh and so forth. Furthermore, granulation at the above roll pressure causes no dust problems, and solubility in a polyolefin resin is also good.

INDUSTRIAL APPLICABILITY

The present invention makes it possible to greatly lower the melting point of a diacetal and to promote its dispersibility in polyolefin resins. As a result, the present invention increases the rate of dissolution in various liquids and molten polyolefin resins, enables lower temperature dissolution and shorter dissolution time, and also dramatically reduces the amount of undissolved matter, which greatly improves product quality and productivity.

Also, when the composition is used as a polyolefin resin nucleating agent, in addition to the effects mentioned above, processing at a lower temperature not only suppresses yellowing and sublimation of the diacetal composition, but also gives a polyolefin resin molding having good transparency and excellent appearance.

What is claimed is:

1. A granular or powdery diacetal composition comprising:

(A) at least one diacetal represented by the formula (1)

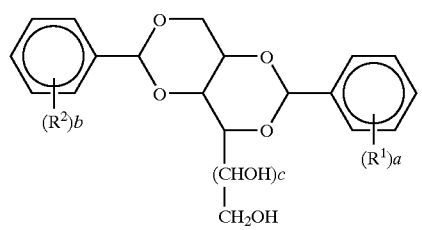

(1)

wherein $R^1$ and $R^2$ are the same or different and each represent a hydrogen atom, a $C_1$ to $C_4$ alkyl group, a $C_1$ to $C_4$ alkoxy group, a $C_1$ to $C_4$ alkoxycarbonyl group or a halogen atom; a and b are each an integer of 1 to 5; c is 0 or 1; when a is 2, the two $R^1$ groups taken together with the benzene ring to which they are linked may form a tetralin ring; and when b is 2, the two $R^2$ groups taken together with the benzene ring to which they are linked may form a tetralin ring;

(B) at least one anionic surfactant, selected from the group consisting of:

a saturated or unsaturated aliphatic alcohol sulfuric ester salt represented by the formula (a):

(a)

wherein $R^a$ is a $C_6$ to $C_{30}$ saturated or unsaturated aliphatic group, and M is Li, Na, K or $NH_4$;

a polyoxyethylene alkyl or alkenyl ether sulfuric ester salt represented by the formula (b):

(b)

wherein $R^b$ is an alkyl group ($C_8$ to $C_{22}$), or alkenyl group ($C_8$ to $C_{22}$), m is an integer of 1 to 8, and M is Li, Na, K or $NH_4$;

a polyoxyethylene alkylphenyl ether sulfuric ester salt represented by the formula (c):

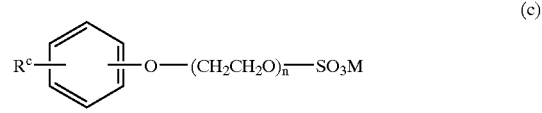

(c)

wherein $R^c$ is an alkyl group ($C_8$ to $C_{22}$), n is an integer of 1 to 8, and M is Li, Na, K or $NH_4$;

a sulfuric ester salt of a polyhydric alcohol fatty acid partial ester formed from a $C_3$ to $C_6$ polyhydric alcohol and a $C_8$ to $C_{22}$ saturated or unsaturated fatty acid, and $C_8$ to $C_{22}$ saturated or unsaturated fatty acid monoalkanol ($C_2$ to $C_6$) amide sulfuric ester salt, wherein the salt is selected from the group consisting of a lithium salt, sodium salt, potassium salt and ammonium salt; and (C) at least one aliphatic monocarboxylic acid optionally having at least one hydroxyl group in the molecule, components (B) and (C) being uniformly dispersed in the particles of the granular or powdery diacetal composition, and component (B) being present in an amount of 0.1 to 3 wt % and component (C) being present in an amount of 0.3 to 5 wt %, and the total amount of component (B) and component (C) being not more than 7 wt %, based on the diacetal composition.

2. The diacetal composition according to claim 1, wherein the weight ratio of component (B): component (C) is 1:0.3 to 4.

3. The diacetal composition according to claim 1, wherein component (C) is a $C_{10}$ to $C_{32}$ aliphatic monocarboxylic acid.

4. The diacetal composition according to any one of claims 1 to 3, wherein component (B) is at least one member selected from the group consisting of lauryl sulfate salts, stearyl sulfate salts, oleyl sulfate salts, polyoxyethylene lauryl ether sulfate salts in which the number of moles of ethylene oxide added is 2 to 3, polyoxyethylene stearyl ether sulfate salts in which the number of moles of ethylene oxide added is 2 to 3, polyoxyethylene nonylphenyl ether sulfate salts in which the number of moles of ethylene oxide added is 2 to 3, polyoxyethylene dodecylphenyl ether sulfate salts in which the number of moles of ethylene oxide added is 2 to 3, monolauric acid glyceryl sulfate salts, monostearic acid glyceryl sulfate salts, lauric acid monoethanolamide sulfuric ester salts, stearic acid monoethanolamide sulfuric ester salts, and oleic acid monoethanolamide sulfuric ester salts, wherein the salt is selected from the group consisting of a lithium salt, a sodium salt and a potassium salt.

5. The diacetal composition according to any one of claims 1 to 3, wherein component (C) is at least one aliphatic monocarboxylic acid selected from the group consisting of capric acid, lauric acid, myristic acid, palmitic acid, stearic acid, 12-hydroxystearic acid, isostearic acid, eicosanoic acid, behenic acid, docosahexanoic acid, montanic acid, oleic acid, linoleic acid, linolenic acid, eleostearic acid, ricinoleic acid, and erucic acid.

6. The diacetal composition according to claim 1 or 2, wherein component (A) is at least one member selected from the group consisting of 1,3:2,4-O-dibenzylidene-d-sorbitol, 1,3:2,4-bis-O-(p-methylbenzylidene)-D-sorbitol, 1,3:2,4-bis-O-(p-ethylbenzylidene)-D-sorbitol and 1,3:2,4-bis-O-(3,4-dimethylbeflzylidene)-D-sorbitol, component (B) is at least one member selected from the group consisting of lithium lauryl sulfate, sodium lauryl sulfate, potassium lauryl sulfate, lithium polyoxyethylene lauryl ether sulfate in which the number of moles of ethylene oxide added is 2 to 3, sodium polyoxyethylene lauryl ether sulfate in which the number of moles of ethylene oxide added is 2 to 3, and potassium polyoxyethylene lauryl ether sulfate in which the number of moles of ethylene oxide added is 2 to 3, and component (C) is at least one member selected from the group consisting of lauric acid, palmitic acid, myristic acid, stearic acid, 12-hydroxystearic acid and oleic acid.

7. A polyolefin resin nucleating agent comprising the diacetal composition according to any one of claims 1 to 3.

8. A polyolefin resin composition prepared by blending a polyolefin resin with the polyolefin resin nucleating agent according to claim 7.

9. The polyolefin resin composition according to claim 8, wherein the polyolefin resin nucleating agent is present in an amount of 0.01 to 5 weight parts per 100 weight parts of the polyolefin resin.

10. A polyolefin resin molded product obtained by molding the polyolefin resin composition according to claim 8.

11. A polyolefin resin molded product obtained by molding the polyolefin resin composition according to claim 9.

12. The polyolefin resin molded product according to claim 10, substantially free from undispersed nucleating agent.

13. A method for manufacturing polyolefin resin pellets, comprising uniformly agitating a mixture comprising a polyolefin resin and the polyolefin resin nucleating agent according to claim 7, at a temperature that is not lower than the melting temperature of the polyolefin resin and not higher than the melting point of the polyolefin resin nucleating agent, to produce a melt, and pelletizing the melt to produce said polyolefin resin pellets.

* * * * *